United States Patent
Warren

(10) Patent No.: US 7,591,835 B2
(45) Date of Patent: Sep. 22, 2009

(54) METHOD AND DEVICE FOR MENDING SKIN OPENINGS

(75) Inventor: Peter D. Warren, Cannes (FR)

(73) Assignee: ExoPatents Marketing Ltd., London (FR)

( * ) Notice: Subject to any disclaimer, the term of this patent is extended or adjusted under 35 U.S.C. 154(b) by 0 days.

(21) Appl. No.: 11/970,085

(22) Filed: Jan. 7, 2008

(65) Prior Publication Data
US 2009/0177227 A1 Jul. 9, 2009

(51) Int. Cl.
A61B 17/08 (2006.01)
(52) U.S. Cl. .................... 606/217; 606/213
(58) Field of Classification Search ......... 606/213–217; 602/41
See application file for complete search history.

(56) References Cited

U.S. PATENT DOCUMENTS

| | | | | |
|---|---|---|---|---|
| 1,452,372 A * | 4/1923 | Gomez | ............. | 606/217 |
| 2,012,755 A * | 8/1935 | De Muth | ............. | 606/217 |
| 2,665,467 A * | 1/1954 | Bosomworth et al. | ......... | 24/400 |
| 2,873,741 A * | 2/1959 | Shearman | ............. | 606/217 |
| 3,260,261 A * | 7/1966 | Gallovich | ............. | 128/889 |
| 3,516,409 A * | 6/1970 | Howell | ............. | 606/217 |
| 4,114,624 A * | 9/1978 | Haverstock | ............. | 606/167 |
| 4,243,038 A | 1/1981 | Harnick | | |
| 4,881,546 A * | 11/1989 | Kaessmann | ............. | 606/217 |
| 4,905,694 A * | 3/1990 | Will | ............. | 606/217 |
| 5,040,274 A * | 8/1991 | Keech | ............. | 24/381 |
| 5,067,207 A * | 11/1991 | Semons | ............. | 24/381 |
| 5,085,663 A * | 2/1992 | Tarr | ............. | 606/172 |
| 5,181,905 A * | 1/1993 | Flam | ............. | 602/41 |
| 5,377,695 A * | 1/1995 | An Haack | ............. | 128/888 |
| 5,396,685 A * | 3/1995 | Wilk | ............. | 24/390 |
| 5,991,980 A * | 11/1999 | Meager | ............. | 24/400 |
| 2001/0008672 A1* | 7/2001 | Norvell et al. | ............. | 428/90 |
| 2002/0091347 A1* | 7/2002 | Eakin | ............. | 602/41 |
| 2004/0180998 A1* | 9/2004 | Gonzales et al. | ............. | 524/109 |

* cited by examiner

*Primary Examiner*—(Jackie) Tan-Uyen T Ho
*Assistant Examiner*—Son Dang
(74) *Attorney, Agent, or Firm*—Michael J. Mehrman; Mehrman Law Office P.C.

(57) ABSTRACT

A zipper-type wound closer attachable to the skin around a skin opening and zipped closed to pull the skin opening closed. The wound closer includes two elongated connecting strips whose feet are pre-coated with adhesive and attached to the skin around the skin opening. The edges of the wound are trimmed flush with the interior sides of connecting strips, and the strips are then zipped together by moving a slider along the connecting strips to join the strips together like a familiar zipper. The wound zipper forms a continuous, toothless seam to prevent seepage of fluid through the seam. By holding the freshly trimmed edges of the skin opening together immobile in a clean, firm, closely aligned connection, the wound closer recreates the conditions under which scar-free healing of the skin can occur naturally; useful for repairing wounds and removing existing scars.

7 Claims, 6 Drawing Sheets

METHOD AND DEVICE FOR MENDING SKIN OPENINGS

TECHNICAL FIELD

The present invention relates to medical devices and, more particularly, to a method and device for closing and promoting scar-free healing of skin openings, such as cuts, wounds and surgical incisions.

BACKGROUND OF THE INVENTION

It is an observable fact that some skin wounds leave scars while others heal leaving minimal scars or no visible scar at all. Even apparently serious wounds, such as a deeply cut finger or a puncture wound through the flesh, sometimes heal without leaving any scar detectable to the naked eye. In some cases, even the closest inspection only a short time afterwards shows no trace of the wound. To prove this assertion, it is sufficient to closely inspect one's own fingers where a cut was known to have occurred some time ago, and be unable to find a scar. This can also be demonstrated by stabbing a fleshy part with the point of a scalpel or lance, as is sometimes done by spring loaded lances used to produce bleeding for coagulation or blood sugar tests, and then attempting to find the cut area some two or three weeks later. Further, most clean needle injections leave no trace some time afterwards, although the skin was cut by the end of the needle (needle tips are constructed as small blades that actually cut the skin).

However, it is equally observable that some injuries and operations, such as surgical intervention for abdominal or thoracic problems, usually do leave unsightly and sometimes disfiguring scars. Scars from thyroid operations and breast reduction or enlargement surgery are seen as both practically inevitable and particularly unsightly. In most cases, coming out from a major laceration or surgical operation without a disfiguring scar is a rarity. It is an observable fact that in the case of many injuries and most operations, by the time the wound is closed and the skin joined back together, the edges of the skin have been handled or exposed to air for some time, often hours, and have long ago ceased to bleed, which indicates that the blood supply to the edges of the skin has been closed off. In effect, after a wound has been open long enough for the bleeding at the edges of the skin to have stopped naturally, the edges of the wound are bordered by dead tissue that is not receiving a blood supply.

In fact, it is almost always part of surgical procedure to "stop the bleeding" using various measures designed to stop the bleeding that does occur. These procedures can include cauterization (burning), which most definitely produces an area of dead tissue wherever it is applied to the wound. Thus, with accepted standard surgical practices, the edges of the skin opening that are not bleeding and hence are no long truly "alive," are joined together when the wound is closed with stitches or staples. In the state in which the wound is left to heal, the finished repair often resembles a series of hills and valleys. Where staples are used, it is not even the dried edges of the skin that are held together, but the undersides of the two edges of skin, which do not normally touch one another (in the absence of such a procedure), that are held to one another by the staples. When a wound is left to heal in this state, a scar always does occur and is often dramatic. All too often, when the staples are removed, an unsightly ridge of fibrous tissue is left as part of the unsightly scar. Despite known situations in which skin openings can and do heal naturally and invisibly under certain circumstances, conventional medical wisdom accepts that other wounds cannot heal without leaving significant, permanent and often disfiguring scars.

Hence, there remains a need for an effective and inexpensive method and device by which skin openings, such as cuts, wounds and surgical incisions, can routinely be closed in such a manner as to create the conditions under which nature routinely proves its ability to produce scar-free healing.

SUMMARY OF THE INVENTION

The present invention meets the needs described above in a wound closer that makes it quick and easy to create the conditions under which the body is capable of scar-free healing. The wound closer includes a first elongated connecting strip configured to adhere to the skin on a first side of a skin opening. The first connecting strip has a first inner face configured to permit a knife to pass along the first inner face to trim the skin adhered to the first connecting strip flush with the first inner face. The wound closer also includes a second elongated connecting strip configured to adhere to the skin on a second side of the skin opening. The second connecting strip has a second inner face configured to permit a knife to pass along the second inner face to trim the skin adhered to the second connecting strip flush with the second inner face. To close the skin opening, the wound closer has a slider that slides along the first and second connecting strips to zip the connecting strips together to form a seam with the first inner face held adjacent to the second inner face and the skin trimmed along the first and second inner faces held together in a butt-joined relation to promote scar-free healing of the skin opening.

In those wounds that heal naturally and unaided and are yet invisible after they have healed, three observable conditions exist. The first condition is that the edges of the skin, while they are cut, are not otherwise damaged, and it may be presumed that those cells at the very edge of the wound are alive and well. Additionally, the edge bleeds profusely, showing that it has a good operating blood supply, something that might be supposed to be desirable or necessary for good healing and without which the cells at the two edges of the wound cannot be well nourished and survive well. The second observable condition of wounds that heal invisibly is that the edges of the wound very neatly butt-join one another without ridges, bumps or gaps, much as two precisely parallel pieces of wood can be placed together edge to edge and result in a join that is almost invisible. If any surface blood is wiped away from such a fresh and neatly joined wound, the joint is sufficiently precise that it is difficult to even see the wound in the absence of blood seepage. Thirdly it is observable that little or no movement occurs between the joined cut skin edges while healing is occurring. Where these three conditions occur naturally—(1) fresh, clean, undamaged, bleeding edges to the wound that are (2) neatly butt-joined to one another with (3) little movement during healing—for example, as in a finger being quite deeply cut with a razor blade—if the blood is wiped away from the cut, it can be difficult to see the cut even though it only happened seconds ago, indicating that there is a very good join between the two cut and bleeding (alive) edges, and further indicating that the edges of the cut closely mate with one another in a very fine line and it is observable that the cut edges are still in relation to one another—there is little or no movement occurring between the joining edges. After a few days, wounds that heal under these conditions are often undetectable to the naked eye.

Experiment has shown that conventional wisdom is not correct and that the conditions required for scar-free healing can be produced albeit with tedious manual procedures consisting of careful trimming and micro-stitches combined with bigger and wider stress-relieving stitches. The wound closer of the present invention provides a relatively simple and inexpensive but highly effective way to automate the creation of those conditions without the tedious manual processes used in the past. When the wound closer is used in its intended manner, it creates the very same conditions that are known to result in scar-free healing with no medical intervention, and that are also known to result in scar-free healing when intentionally reproduced mechanically.

To produce these same conditions, the wound closer is designed to mend a wound and promote scar-free healing by 1) bringing together fresh and alive skin edges, 2) in a precise edge-to-edge butt joint to heal before clotting or drying or cell death has set in on the edges of the wound, and 3) holding the edges of the wound together in a neatly joined relationship without movement for long enough for healing to occur, these being the conditions under which the body is able to produce scar-free healing naturally. No further manipulation or subsequent removal of scar tissue is required. In view of the natural elastic ability of the skin to stretch to a considerable extent, the wound closer can be used to close skin openings from small to quite large surgical incisions associated with major operations, such as abdominal surgery or under conditions where skin loss has occurred. The wound closer, therefore, represents a relatively simple and inexpensive device that is faster to use and less invasive than conventional stitching and which can be easily applied to wounds from small to quite large to close skin openings in an manner that promotes scar-free healing. As such, the invention represents a major and much needed breakthrough in skin closing technology.

The invention solves the problems described above by using an elongated, self-adhesive and sometimes lozenge-shaped wound closer that is attached with suitable adhesive to the skin around the skin opening such that the wound itself and some skin (skin that must be undamaged) remain within the opening enclosed by the wound closer. Scar-free healing conditions are created by trimming off the excess skin inside the wound closer opening, which also removes all dead and all damaged skin, by cutting away the skin along the inside edges of the wound closer, typically by using a knife or blade that is guided by the wound closer itself or by a knife guide located on the wound closer. Immediately after trimming the wound, and without taking any measures to stop the bleeding, the wound closer is zipped closed. The result is that newly cut edges of the skin are brought and held together by the wound closer in a clean, closely aligned butt-joint connection between freshly trimmed (and hence alive) edges of the skin, thereby promoting scar-free healing of the skin opening.

The wound closer typically includes two elongated connecting strips each with significant flange surface covered with adhesive coating that attaches to the skin adjacent to the skin opening and once attached, the edges of the wound are trimmed along the inner faces of the connecting strips and flush with the inner faces of the connecting strips, and the strips are then zipped together by moving a slider along the connecting strips to join the strips together like a familiar zipper. This pulls the skin opening closed under the joined wound closer, and the wound closer preferably (when closed) forms a continuous, toothless seam to prevent seepage of fluid into the wound through the seam.

A first advantage is that the wound closer is faster and simpler and quicker to apply than stitching up a wound. Another advantage of the wound closer is that (because no deeply penetrating stitches are required) nerve blocking anesthetic injections required by stitching may not be necessary and spray-on anaesthetic or anaesthetic embedded in the adhesive may suffice to enable painless trimming. Another advantage is that it can produce wounds that repair with no visible scar, no matter the length of time the wound has been open, nor the roughness of the manipulation to which the skin bordering the wound has been subject. In the case of females with facial wounds, this advantage is considerable. Another advantage is that the invention can theoretically be applied at home in the case of minor injuries (where no trimming is required to produce wound edges that join precisely or when spray-on anesthetic or anesthetic embedded in the adhesive suffices) when such injuries would normally require a trip to the doctor and stitching. Another advantage is that if packaged together with a local anesthetic patch, spray-on anesthetic, or adhesive strip embedded anesthetic, a wound closer can be applied by emergency personnel in difficult situations where no doctor is available.

A further advantage is that a suitably modified wound closer, without trimming the skin, can be used to hold wounds closed in emergency situations, and help stop bleeding by closing the edges firmly, which can sometimes be difficult to do with bandage systems. Another advantage is that the wound closer can be removed by anyone and does not require a second trip to the doctor to "remove the stitches" a procedure that can also be painful. A further advantage is that stitches that are normally used penetrate the skin sometimes themselves become infected, but since the wound closer does not penetrate the skin this risk is avoided. A further advantage of this invention is that existing scars can be removed by using a big enough wound closer to enclose the skin with the scar in it, then cutting out the skin containing the scar in the standard manner described above and then closing the wound closer. Another advantage of the method is that it permits wound closers to be manufactured in various shapes to confirm to curvatures of the body such as over an eyebrow, or curved wounds, such as commonly occurring round a nipple as a result of breast surgery. Another advantage of the invention is that it permits wound closers to be manufactured in different configurations such as one-piece units pre-joined at the ends complete with zipping device, or as continuous strips on reels that can be cut to length required, and then separated as required to provide a long enough opening for the wound in question (and then used with a separate closing tool), or as wound zips with narrower or wider feet and hence larger or smaller adhesive surfaces to suit the anticipated skin stress at the repair site.

Generally described, the invention may be practiced as a wound closer that may optionally include an associated knife or knife blade that function together as a method for closing wounds quickly and easily doing so in a fashion to promote scar-free healing of a skin opening. The wound closer includes a first elongated connecting strip whose foot carries a first adhesive surface, a second elongated connecting strip whose foot carries a second adhesive surface, and a slider configured to slide along the first and second connecting strips to zip the connecting strips together. The first and second adhesive surfaces are configured to adhere to the skin adjacent to the skin opening and pull the skin opening closed as the slider zips the connecting strips together in a manner similar to that which occurs with zip-lock bags, but in this case as a permanent one-time closure. The connecting strips, when zipped together, preferably form a continuous, toothless water-tight seam to prevent seepage of fluid through the seam. The connecting strips may connected directly to the skin or they may be carried on an adhesive bandage having a width selected to be suitable for the particular wound to be closed.

The wound closer may be configured to work with a specially designed knife or knife blade, which is configured to slide along a knife guide disposed along the interior edge of the connecting strip. While trimming may be done with an ordinary scalpel using the foot of the connecting strip as a guide, the optional specially designed knife or knife blade ensures that the skin can be trimmed with the necessary closeness to the inside face of the connecting strip, without at the same time cutting and damaging the connecting strip itself. More specifically, the knife guide may be configured to receive a guide follower on a knife or knife blade that is specially designed to be used in connection with the knife guide and has the effect of both regulating the depth of the cut, and cutting the skin flush with the inward-looking face of the connecting strip. For example, the knife guide may be an elongated channel extending along the connecting strip, and the guide follower may be a tab configured to be received within and slide along the channel. In addition, each connecting strip or a bandage adhered to the connecting strip (or both) may be formed from a microporous substrate configured to allow passage of air and block inward passage of potentially contaminating liquids, and either or both may carry an impregnated antibiotic, anaesthetic or other medically active substances.

To close and promote scar-free healing of an opening in living skin tissue, a wound closer is adhered to the skin around the opening. Specifically, the first elongated connecting strip is adhered to the skin adjacent to a first side of the skin opening, and the second elongated connecting strip adhered to the skin adjacent to a second side of the skin opening. A knife is then used to trim the skin along and flush with the inner edges of the first and second connecting strips. Very promptly after trimming, and without first stopping the bleeding that results from trimming, the connecting strips are zipped together by sliding the slider along the connecting strips to fasten the connecting strips to each other and thereby pull the skin opening closed. To further secure the seam formed by the connecting strips, a seam sealer may be used to clamp or set or cure an adhesive in the seam. For example, an adhesive may be deployed in the seam that cures or sets in response to energy applied to the seam, for example by an electrical sealing device that may be slid along the seam or by a device that applies UV or microwave energy to the seam to cause the adhesive to set. However, any such energy source used in additional sealing should be so configured so as to avoid delivering damaging energy to the wound itself and causing (for example) undesirable blood coagulation or other wound damage. Additionally, the adhesive or the substance of the wound closer itself, or both may be constructed so as to change the color in response to passage of time (indicating the wound is healed) or to closing the wound closer properly, or to energy applied to the adhesive indicating the adhesive is cured and set, or to any of these, or differently to any selection of these.

In view of the foregoing, it will be appreciated that the present invention provides a cost effective and rapid wound closing device for closing wounds and promoting scar-free healing of skin openings.

DETAILED DESCRIPTION OF THE EMBODIMENTS

Figure 1:
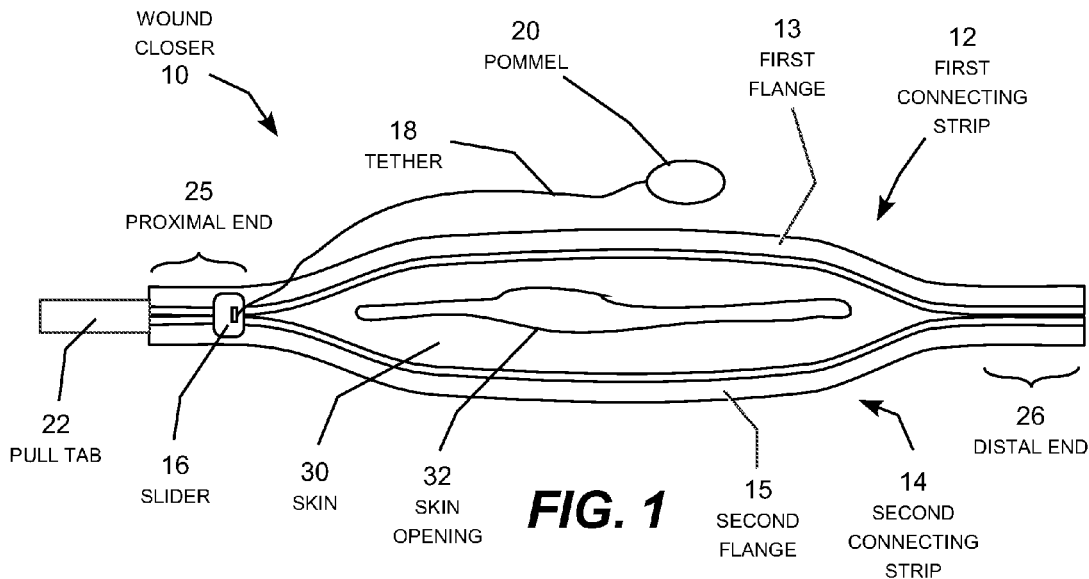
FIG. 1 is a top view of a wound closer that includes elongated connecting strips adhered to the skin around an untrimmed wound and a slider for zipping the strips together.

The present invention may be embodied in a zipper-type wound closer known as the WoundZip™, which is used to close skin openings, such as cuts, wounds and surgical incisions. The wound closer, which is typically supplied sterilized in a sterile package, consists of a pair of hard but pliable joinable connecting strips that form a zipper that can be joined together by moving a slider along the connecting strips. The connecting strips include adhesive coated flange surfaces that enable the connecting strips to be adhered to the skin surrounding the wound. As an alternative to provide additional surface for skin adhesion, the connecting strips may be adhered to and carried on a suitably sized adhesive bandage. In either configuration, the connecting strips are adhered sufficiently firmly to the skin to allow the wound closer to pull the skin opening closed, and hold the edges of the skin opening together at a neat, freshly cut butt-joint, for a sufficient period of time, typically several days to 2 weeks, to promote scar-free healing.

The preferred zipper is a durable, firm plastic structure that forms a continuous, water-tight, toothless seam that protects the wound from blows, prevents flexing that could break the healing-in-progress and acts to prevent fluids from reaching the wound through the seam. When used properly, the wound closer brings the skin opening together in a manner that reproduces the conditions needed to allow natural healing processes to produce invisible, scar-free repair of cuts and wounds, without disfiguring scars that occur in the state of the art and characterize wounds from minor or major injury or surgical operations.

In practical use, prior to using the wound closer, the area concerned is locally anaesthetized in an appropriate manner (unless the wound closer is constructed to be self-anaesthetizing), all foreign matter and hair is removed and the surrounding skin and the wound itself are cleaned and disinfected as per usual practice preparatory to stitching. The wound closer is then removed from its sterile packing and attached to the skin around the wound so as to enclose the wound within the elongated opening between the connecting strips. The skin is then trimmed flush to the internal edges of the connecting strips of the wound closer. Without using any measures to stop bleeding, the two halves of the wound closer are immediately locked together by pulling the closing slider down the length of the wound closer (while holding the pull tab to prevent the wound closer from moving) thereby zipping the two halves of the wound closer together, and hence bring the freshly trimmed edges of the skin opening together also without need to use stitches, and bringing them together as a clean, well aligned seam and then holding them in that correct relationship long enough to enable scar-free invisible healing to occur naturally.

Describing the invention in further detail, the wound closer consists of paired connecting strips that are separated from one another except at either end where they are already joined together (with the slider located at one end) thereby leaving an elongated opening that can be positioned so as to surround the cut to be closed. The vertical interior faces of the connecting strips that touch one another when the wound closer is closed, together with the construction and substance of the wound closer itself are such that, when closed, the connecting strips hold the two halves of the trimmed wound (and hence the skin attached to them) flat in relation to one another. The connecting strips of the wound closer may also be provided with drainage channels and may also be constructed with a suitable opening though which a drainage tube may pass, so that most of a wound may heal, while a drainage tube passes through part of the wound to drain fluids from the interior of the body. The wound closer may also be placed over a drainage tube, which is held firmly in place by a suitably constructed wound closer. Once the drain is removed, the drain hole may be closed by using another wound closer in the described manner.

Both sides of the molded connecting strips have a lower flat surface or foot that is presented to the skin which is covered by a strong adhesive (protected by a film that is removed prior to use). The foot has to be wide enough and the adhesive used strong enough to pull the skin opening closed as the connecting strips are zipped together. From the time the wound closer is closed, the adhesive must then be strong and durable enough both to hold the wound closed for the seven to ten days healing requires, and also to transmit the sheering or other forces to which the surrounding skin is subject entirely to the wound closer itself so that the wound closer can protect the wound that is healing from forces that could break the natural repair that occurs and so prevent the scar-free healing. With an adequate adhesive, the wound closer can then protect the wound and, for a sufficiently long period of time, consistently hold the edges of the healing skin in a stress-free zone, in the precise relationship they need, long enough for them to heal without a visible scar.

Once the wound has had time to heal, the adhesive must be such that the wound closer can be removed (without unzipping it or tearing the skin or the newly-closed wound) potentially with a suitable solvent to dissolve the adhesive. The adhesive may also be so constructed as to deteriorate automatically so that the wound closer comes off of its own accord after a suitable healing period. Adhesives similar to those used on typical medical bandages and tapes are believed to be suitable for these purposes. Optionally the adhesive surfaces of the wound closer or the bandage to which it is attached, or both may be impregnated with a sterilizer, an antibiotic or any other appropriate substances including drugs such as pain killers or a short-lived local anesthetic to enable the skin to be painlessly trimmed as described.

Immediately before closing the skin opening, a knife is used to trim the skin adjacent to and flush along the length of the inside edge of each connecting strip, typically by sliding a knife or knife blade along each connecting strip with is then additionally acting as a knife guide. Optionally the wound closer works with a specially designed knife or trimming scalpel blade that has a protruding guide follower, such as a tab, that engages in a guide, such as a slot, along the interior side of both connecting strips of the wound closer. The depth of blade protruding below the guide is such that the blade is long enough to cut the skin but not underlying tissues and as a result the guide and guide follower result in the skin being cut to a suitable depth, and cut close and flush to the connecting strip, without cutting and damaging the connecting strip itself. Different blades can be provided, or the blade length can be adjusted, so that the blade protrudes enough beyond the guide for particular thicknesses of skin. The blade handle may be a standard scalpel blade holder or a specially designed blade may be supported in a molded, single-use, scalpel-like structure. Regardless of the knife configuration, the blade is used to trim the skin flush with the interior edges of the wound closer without cutting or damaging the interior edges of the wound closer itself. In this way, the skin is newly and cleanly cut and trimmed to match the interior edges of the wound closer immediately prior to closing. This trimming removes all the dead skin at the edge of the wound and all teeth or indents and all damaged skin at the edges of the wound and leaves the edges of the wound as even and gently curved lines ready to be held together in a neat butt-joined manner when the wound closer is closed, much as the two edges of two pieces of wood to be glued are smoothed to remove ridges or gaps before gluing them together.

When trimming is completed the connecting strips of the wound closer are then promptly brought together to close the skin opening before blood clotting or skin edge drying occurs (and without taking any measures to prevent or stop bleeding from the freshly cut edges); the connecting strips are closed together by pulling the pommel that is attached by a tether to the closing slider (or by using a similarly configured closing tool), while holding firmly a flexible pull tab at the opposite end of the wound closer, so as to prevent the wound-zip from moving as the slider is being pulled to close the wound closer. As the slider moves along the top portions of the two halves of the wound closer it joins them together in a similar fashion to the way that the edges of a zip lock bag join together by pressing them together so that the male and female halves engage one another and hold one another firmly together. The slider is pulled until the slider comes completely off, and the pull tab is then cut or torn off the wound closer. Once the wound has had sufficient time to heal the wound closer is removed.

In general, the wound closer used as described above reproduces the conditions that allow natural scar-free healing processes to take place. It will be appreciated that the wound closer can be made in different sizes, lengths and shapes so as to be suitable for different regions of human or animal bodies, and to be suitable for different purposes and suitable to absorb different levels of skin sheering or other stress that may be expected to occur in different bodily regions, the principle always being that the size and strength of the wound closer and its adhesive are together adequate to hold the edges of the wound immobile in relation to one another while they heal.

In alternative embodiments, the connecting strips for the wound closers may be made in male and female halves on separate reels or pre-joined on a single reel and cut to the length on an as-needed basis. In this embodiment, male and female strips are applied to the sides of the wound to be healed, and then the skin of the wound trimmed in the manner already described, close to the interior face each of the two wound connecter strips. In this case, a closing tool that has a closing slider mounted on a handle is used to close the two halves together. If a high amount of stress across the wound zip is to be anticipated, one or more clamps may be put in place by a suitable tool and spaced out along the length of the connecting strips to reinforce the seam of the wound closer.

In another alternative embodiment, particularly where high stress or sheering levels might occur to the wound area, stress may be spread over large areas by using the wound closer in combination with a suitably designed self-adhesive bandage, so that the wound closer is adhered to the bandage and then the bandage, with wound closer attached, is itself adhered to a large skin area round the wound. In this embodiment, a male connecting strip is adhered in a preparation stage to a specially prepared edge of an appropriately designed bandage, and a female connecting strip is adhered in a preparation stage to the upper edge of another piece of the same bandage, and then the ends of the connecting strips are closed together with a closing tool so as to leave a gap in the middle, finally applying this assembly to the wound and trimming and closing the wound as previously described.

The wound closer can also be adapted for use to join materials other than living skin edge-to-edge, so as to repair cuts or join edges of flexible materials such as upholstery or inflatable mattresses and to join both flexible and rigid materials edge-to-edge on a temporary or permanent basis. In this embodiment, adhesives of different types substitute for and replace the natural healing properties of skin. In one such embodiment, with suitable adhesives, the wound closer device can be used to repair cuts or rents in flexible materials such as upholstery, canvas canopies on boats or convertible automobile tops, or inflatable mattresses, or plastic pools, to name just a few examples. The wound closer may either be left in place as a neat looking repair device or used on a temporary basis as a clamp to hold materials together while an adhesive sets. The wound closer may be an attractive alternative to normal repair methods, such as an unsightly patches or stitches, and may perform better because the wound closer provides a better way to hold the edges together in the correct relationship while the adhesive sets in the very area represented by the two edges to be joined. The wound closer invention enables such joins to be made by holding the flexible edges of material to be joined in the correct relationship for long enough for the joining agent or joining processes to work.

The wound closer can also be used in construction, for example to join flexible materials such as panels of a tent, or even non-flexible materials such as wall panels of a display stand. Wound closers of various designs can be used to join panels of material either on a temporary or permanent basis.

Turning now to the figures, in which like numerals refer to like elements throughout the figures, FIGS. 1-4 are a series of top views of a wound closer 10 illustrating use of the wound closer to close a skin opening and promote scar-free healing. Referring to FIG. 1, the wound closer 10 includes a first and second connecting strips 12, 14 that are zipped together by a slider 16 in a manner that is similar to a familiar zipper or zip-lock bag. The first connecting strip 12 includes a zip fastener (shown in more detail in FIG. 10) carried on a relatively wide first flange 13 that is configured to be adhered to the skin in area around a wound. Similarly, the second connecting strip 14 includes a zip fastener carried on a second flange 15. The slider 16 can be moved along the connecting strips 12, 14 from a proximal end 25 to a distal end 26 to zip the connecting strips so as to join the zip fasteners to each other. A tether 18 connected to a pommel 20 may be connected to the slider 16 to facilitate gently pulling the slider along the connecting strips. The wound closer also includes a removable pull tab or handle 22 to hold the proximal end 25 of the wound closer in position while the slider 16 is pulled along the length of the connecting strips toward the distal end 26 to zip the wound closing device closed.

Figure 2:
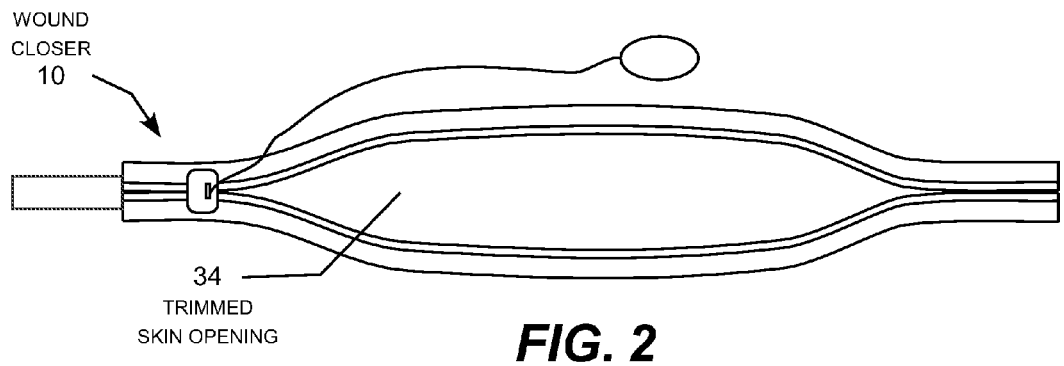
FIG. 2 is a top view of the wound closer after the skin has been trimmed.
Figure 3:
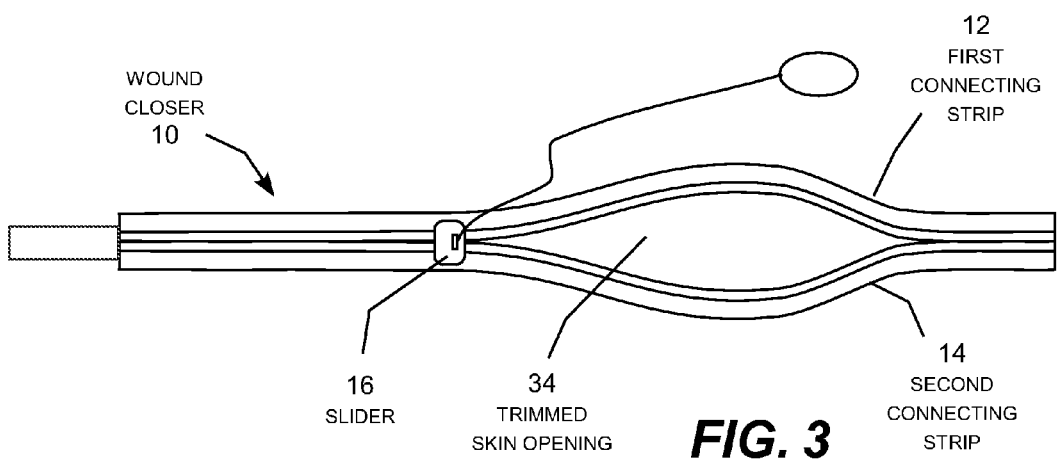
FIG. 3 is a top view of the wound closer after the connecting strips have been partially closed.
Figure 4:
FIG. 4 is a top view of the wound closer after the connecting strips have been fully closed.

The connecting strips 12, 14 are typically joined together to form short lengths of joined connecting strips at the proximal and distal ends 25, 26, with the connecting strips separated from each other along the length between these ends. The slider 16 may be fed onto the proximal end 25 of the connecting strips 12, 14 before the strips are adhered to the skin. The connecting strips 12, 14 are then adhered to the skin 30 around the wound 32. The skin 30 that is inside the wound closer opening is then trimmed along the inner edges of the opening formed by the connecting strips 12, 14, as shown in FIG. 2, to create clean, freshly cut edges of the skin that can be neatly butt-joined to promote scar-free healing by zipping the would closer. As shown in the transitions from FIG. 2 to FIG. 3 and then to FIG. 4, promptly after trimming the skin, the slider 16 is pulled from the proximal end 25 along the length of the connecting strips 12, 14, typically all the way off the distal end 26 of the connecting strips. The pull tab 22 is then cut or snapped away from the connecting strip to leave the neatly zipped seam shown in FIG. 4.

Figure 5:
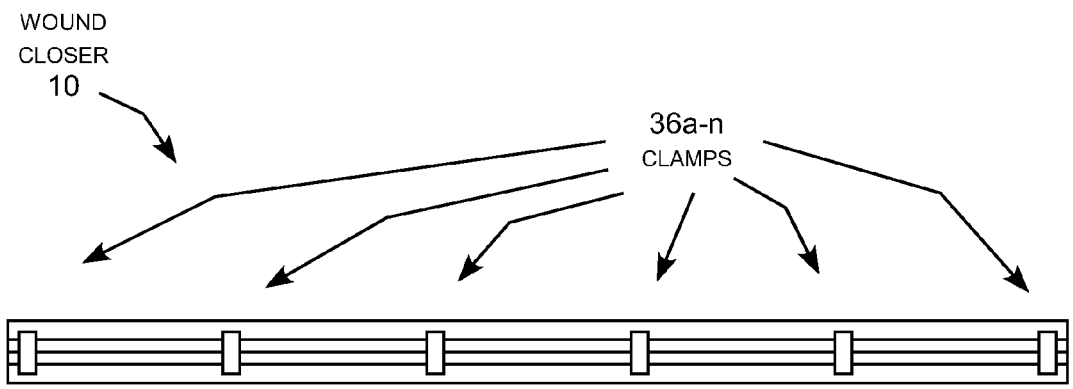
FIG. 5 is a top view of the wound closer after the connecting strips have been fully closed and clamps have been added to strengthen the seam.

Referring to FIG. 5, to strengthen the zipped seam of the wound closer 10 after closing, one or more mechanical clamps 36a-n may be fastened to the seam. For example, these clamps may be small metal clips or staples crimped to the seam with a hand-held stapler or crimping pliers. Alternatively, plastic clamps may be slid along the seam formed by the connecting strips 12, 14 and then glued, melted, cured, tightened by heat shrink technique, or otherwise secured in place. Preferably, the clamps do not cut or pierce the seam, which could undermine the water-tight and sterile condition of the closed seam.

Figure 6:
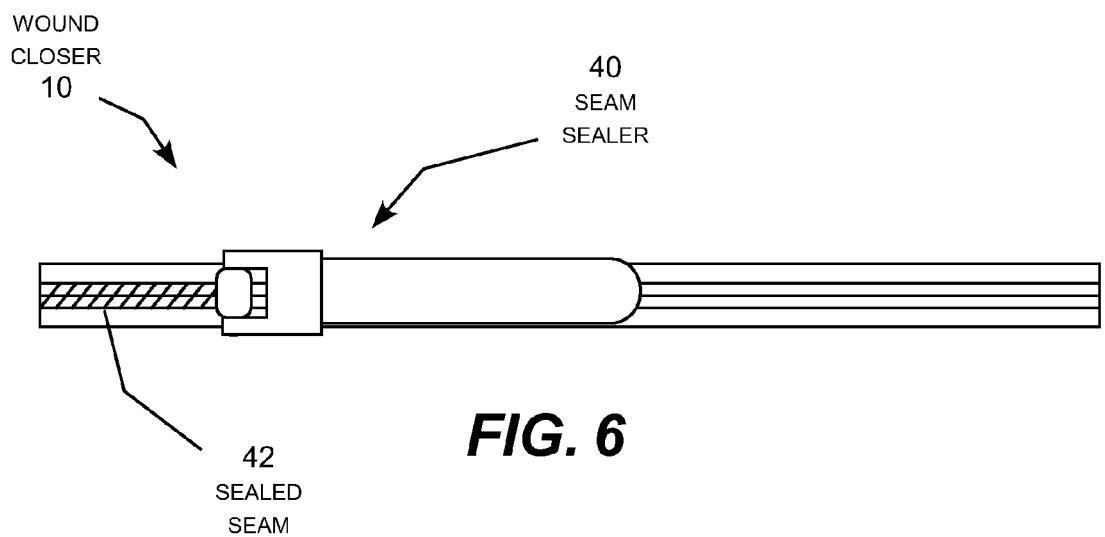
FIG. 6 is a top view of the wound closer after the connecting strips have been fully closed and a seam sealer has been partially applied to seal the seam.

In another alternative shown in FIG. 6 that some people may find to be more attractive and less likely to snag on clothing, a seam sealer 40 may be slid along the seam to set or cure an adhesive in the seam. For example, the seam sealer 40 may include an electric crimping device that applies heat and pressure to set the seam. The electric seam sealer may plug into a household power outlet or be powered from internal batteries, which would be suitable for closing wounds in the field. For example, a battery powered seam sealer would be suitable for deployment in ambulances and other emergence first aid locations. Other types of curing devices, such as ultraviolet light or sonic curing mechanisms may be used. The adhesive in the seam formed by the connecting strips 12, 14 may also change color to indicate that the seam has been properly set or cured. This is particularly helpful with a heat sealing technique to indicate that the seam has been heated sufficiently to set the adhesive.

Figure 7:
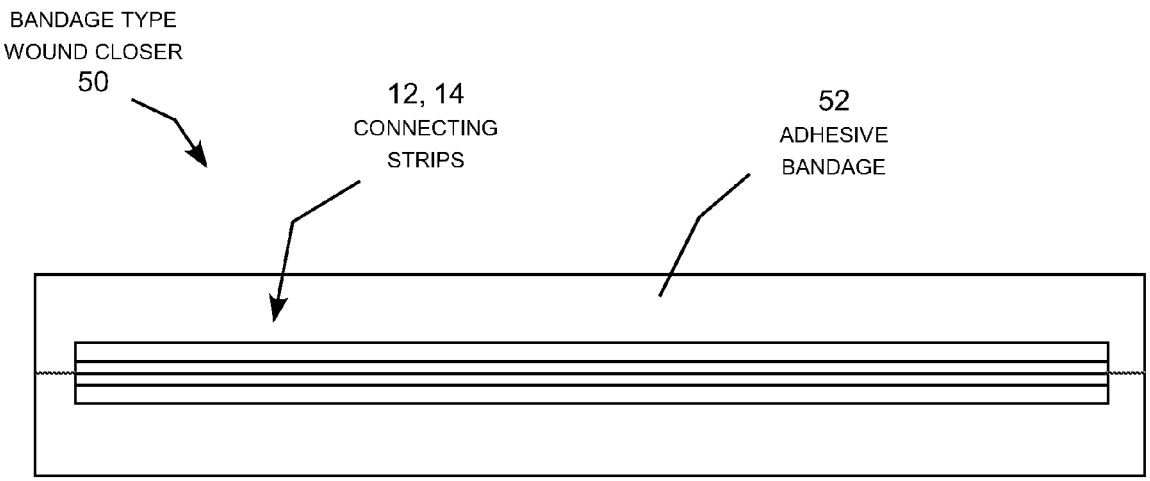
FIG. 7 is a top view of an alternative wound closer that has already been closed and is carried on an adhesive bandage.

FIG. 7 illustrates an alternative wound closer 50, in which the connecting strips 12, 14 are carried on adhesive bandages 52 that provide increased surface area for adhering to the skin. The connecting strips of wound closer 50, with the adhesive bandages 52 underlying and extending well beyond the connecting strips, are adhered to the skin 30 around a skin opening 32 and then zipped together to close the wound in the same manner as described with reference to FIGS. 1-4. The adhesive bandage 52 may be treated with an antibiotic, an anesthetic or another medically useful substance, and may also be formed from a microporous material that allows air to pass but serves as a moisture barrier.

Figure 8:
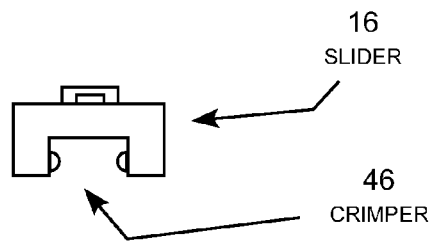
FIG. 8 is a cross-sectional view of the slider of the wound closer.
Figure 9:
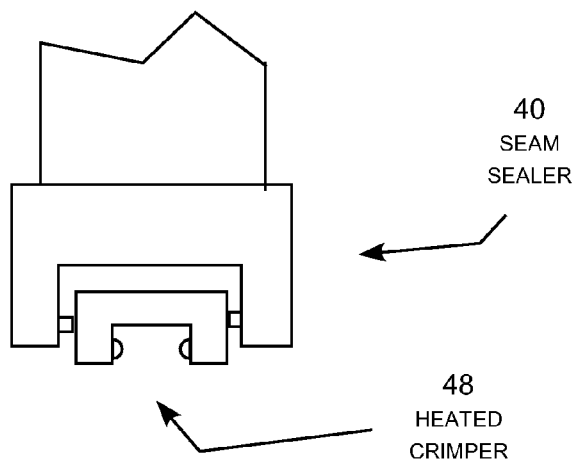
FIG. 9 is a cross-sectional view of the seam sealer.

FIG. 8 is an end view of an illustrative slider 16, which in this example includes a pair of aligned hemispherical protrusions that form a crimper 46 that pinches closed a zip connector in the seam formed by the connecting strips 12, 14 as the slider moves along the connecting strips. FIG. 9 is an end view of an illustrative seam sealer 40, which in this example includes a metal slider pivotally mounted on a handle. In this particular example, the metal slider is electrically heated to form a heated crimper 48. This particular sealing technique is merely illustrative and, as noted previously, other seam sealing techniques may be employed. Nevertheless, it should be appreciated that the electrically heated seam sealing 40 provides a relatively simple seam sealing technique that, together with an adhesive that changes color when it has been heated sufficiently to set the adhesive, results in an inexpensive and effective system for creating continuous, water-tight, highly secure seams.

Figure 10:
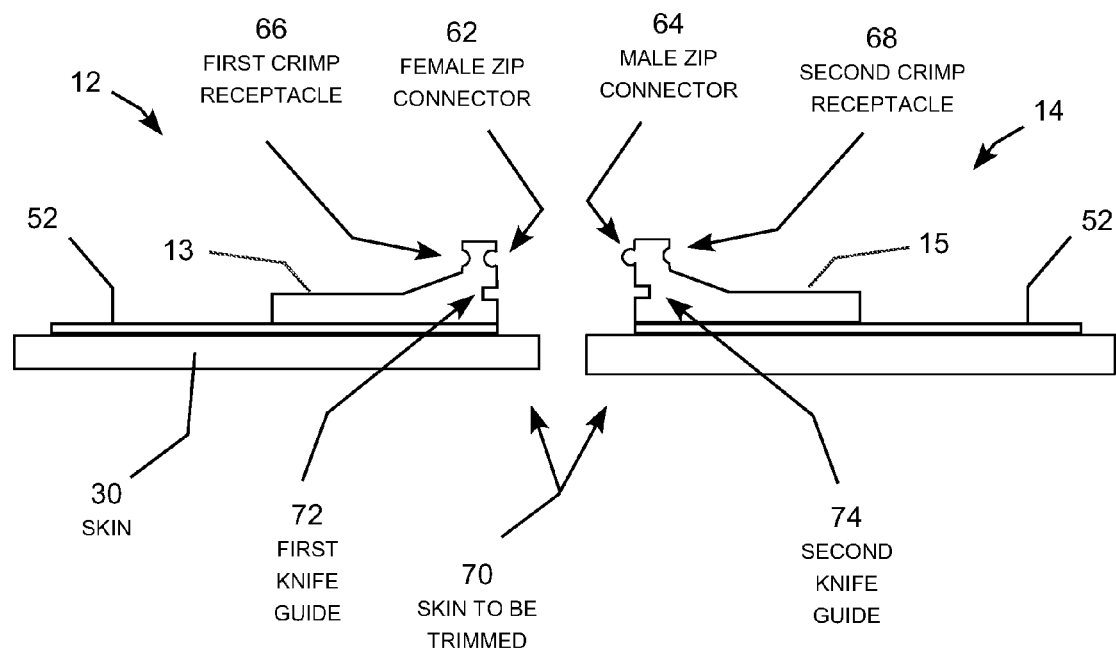
FIG. 10 is a cross-sectional view of the connecting strips of the wound closer that is attached to a bandage in this case.

FIG. 10 is a cross-sectional view of the connecting strips 12, 14 of the wound closer. The first connecting strip 12 includes a relatively wide flange 13 and a female zip connector 62. The second connecting strip 14 includes a relatively wide flange 15 and a male zip connector 64 that is aligned with the female zip connector 62. The first connecting strip 12 also includes a first crimp receptacle 66 aligned with the female zip connector 62, and the second connecting strip 14 includes a second crimp receptacle 68 aligned with the male zip connector 64. The crimp receptacles 66, 68 thus form a grove in which the crimper 46 of the slider 16 travels to pinch the male zip connectors 64 into the female zip connectors 62 to form a continuous, water-tight seam joining the connecting strips together. The clamps 36a-n and the heated crimper 48 are also generally shaped to fit into the grooves formed by the first and second crimp receptacles 66, 68. The specific shape of the male and female zip connectors 64, 62, the first and second crimp receptacles 66, 68, and the surrounding structures are merely illustrative and may be adjusted, as a matter of design choice, to create a suitable zip connector. However, the structures shown are believed to be suitable for creating an inexpensive and effective zip connector suitable for cost effective extrusion manufacturing in bulk. In the example shown in FIG. 10, the connecting strip 12, 14 may each be extruded as a one piece molding.

FIG. 10 shows the connecting strips 12, 14 positioned over wound that includes skin to be trimmed 70 prior to closing the wound. In this particular design, the height of the zip connector extending above the crimp receptacles 66, 68 must be sufficient as to prevent the male and female zip connectors 62, 64 from separating when the underlying tissue exerts upwards or bending force on the flanges 13, 15. It is important that the edges of the skin remain in a neat butt joint after the wound closer is closed. The construction of the would closer therefore prevents upward pressure on either side of the wound closer from causing the flanges 13, 15 to separate after closing.

Figure 11:
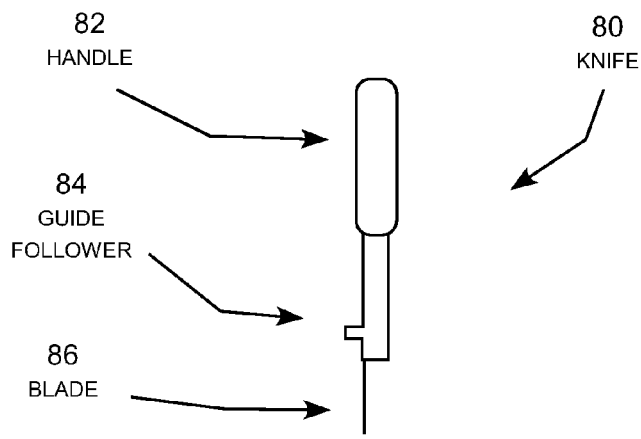
FIG. 11 is a side view of a skin trimming knife configured to work in association with the wound closer.

FIG. 10 illustrates knife guides 72, 74 defined by the connecting strips 12, 14, respectively, that cooperate with a specially designed knife 80 shown in FIG. 11. In this particular example, the knife guide is a channel that extends along the connecting strip a constant distance above the bottom of the connecting strip. The knife guide is configured to receive a guide follower, in this example a tab 84 on the knife 80, which is specifically designed to work with the knife guides 72, 74.

FIG. 11 shows the illustrative knife 80, which includes a handle 82, a guide follower tab 84, and a blade 86. The blade may be of fixed length with a variety of knives of different length provided, or the length that may be adjustable, for example with a worm gear.

The knife guides 72, 74 and guide follower 80 are one example of a suitable, reliable and inexpensive type of knife guide and cooperating guide follower system. Other guide system may be employed. In particular, the knife guide may be any structure added to or formed as part of the connecting strip used to guide a knife to cut the skin underlying the connecting strip. For example, the knife guide can be any suitable type of flat, beveled, rounded or eccentric shaped surface or channel that conforms to the shape of a guide follower on the knife. The guide follower may be as simple as the knife itself or a pair of perpendicular abutment surfaces that slide along the top and inner surfaces of the connecting strip. The inner or top surface of the connecting strip may also be shaped, with a cooperating shape provided on the guide follower, to provide additional registration between the guide and guide follower surfaces to enhance the guiding function. Many different types of knife guides can be designed to work with any appropriately configured guide follower.

The knife guide in combination with the knife follower ideally should provide a positive surface interface that keeps the knife securely against the connecting strip and precisely control the depth of the cut made by the knife blade to ensure a smooth, clean trim of the skin to the correct depth. The channel and tab system of the knife guides 72, 74 and guide follower 84 produce the desired result, but other types of guides may be employed as a matter of design choice. Sliding contact between the knife guide and guide follower, which can be aided by a lubricant, will work well and provide for a low cost system. However, more sophisticated guides, such as those employing rolling contact or supporting a laser or other type of cutting instrument may be employed. The important function of the knife guide and follower is to obtain smooth, clean, freshly trimmed skin edges along and immediately below the connecting strips, which are then brought together in butt-joined relation by zipping the connecting strips together. The seam formed by the connecting strips then become sealed, for example by an adhesive in the seam or with the aid of clamps or a sealing device, to securely maintain the skin edges in butt-joined relation throughout the healing process to promote scar-free healing of the skin opening.

Figure 12:
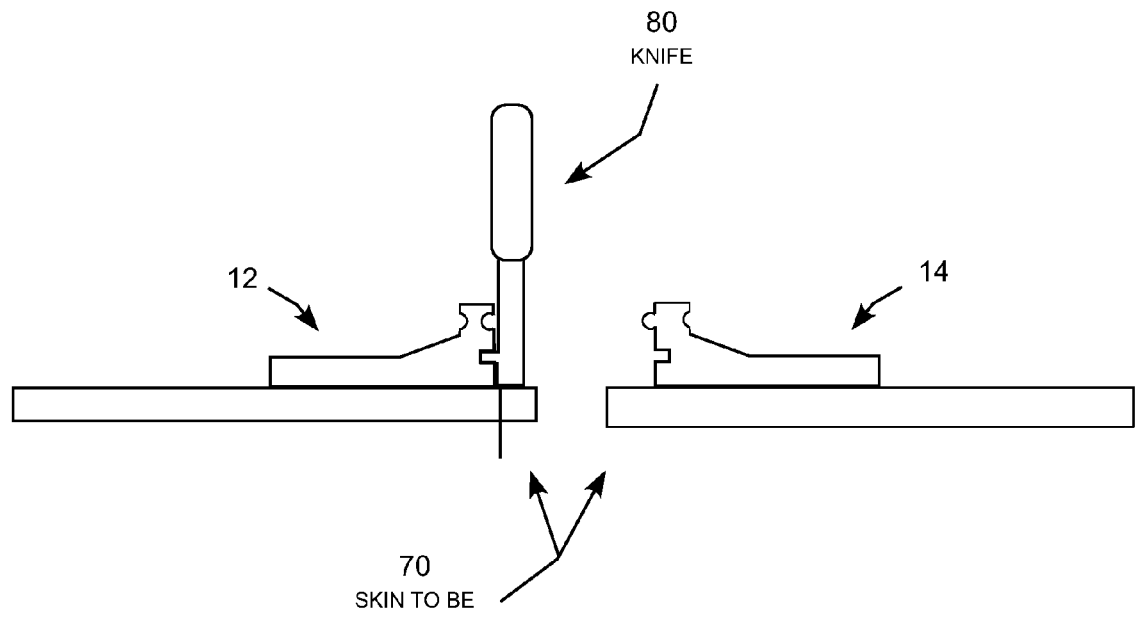
FIG. 12 is a cross-sectional view of the wound closer applied to the skin with the knife positioned to trim the skin along one of the connecting strips.
Figure 13:
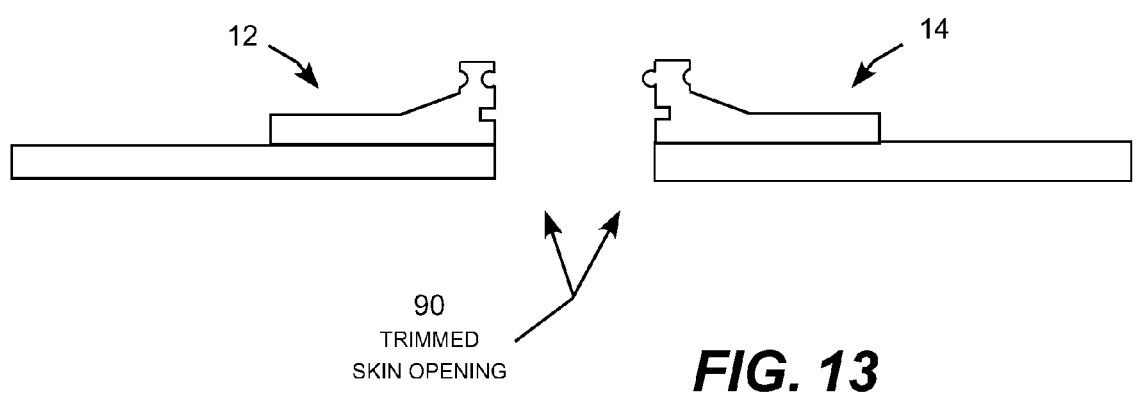
FIG. 13 is a cross-sectional view of the wound closer applied to the skin around a skin opening after trimming.
Figure 14:
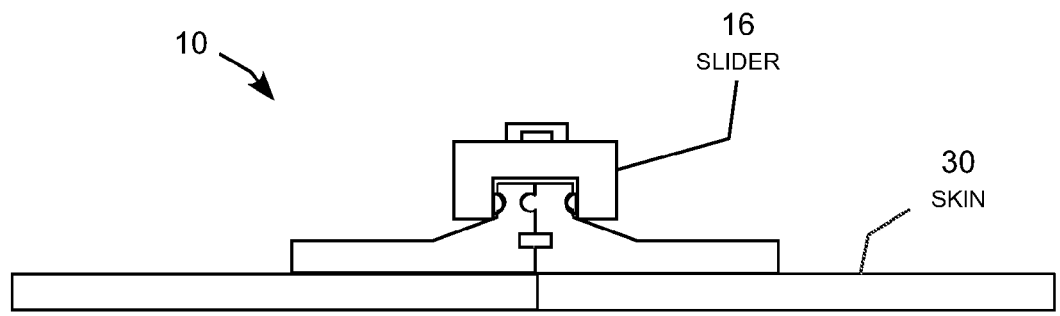
FIG. 14 is a cross-sectional view of the wound closer and slider after the wound closer has been zipped to pull the skin opening closed.
Figure 15:
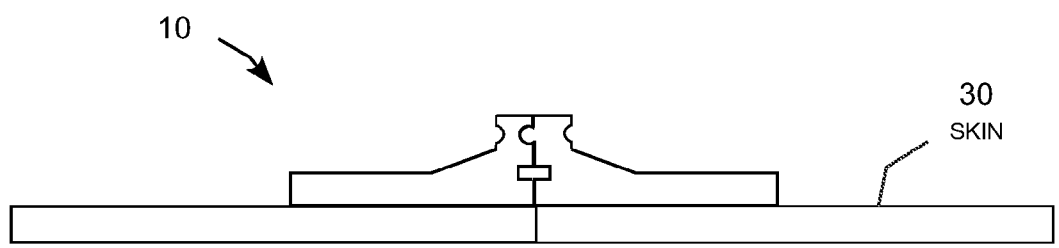
FIG. 15 is a cross-sectional view of the wound closer after the wound closer has been zipped to pull the skin opening closed and the slider removed.
Figure 16:
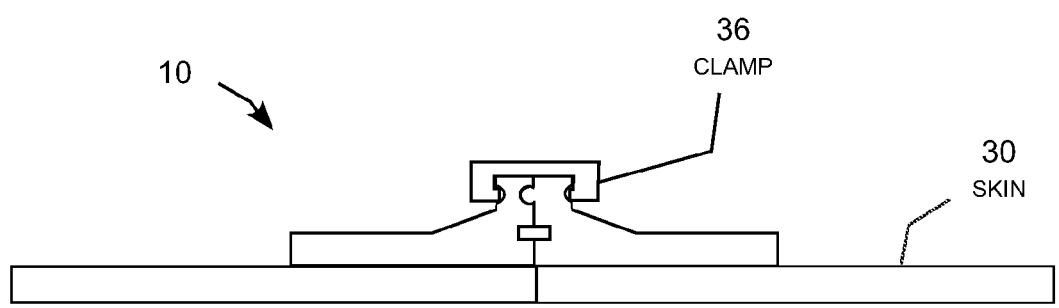
FIG. 16 is a cross-sectional view of the wound closer and slider after the wound closer has been zipped, the slider removed, and a clamp applied to the seam.

FIG. 12 shows the knife 80 positioned in the knife guide 72 of the first connecting strip 12 for skin trimming. The relatively wide flanges 13, 15 of the connecting strips 12, 14 are adhered to the skin with the skin opening positioned within the opening between the connecting strips. The knife 80 shown in FIG. 11 is then used to trim the edges of the skin, as shown in FIGS. 12 and 13. To close the wound closer, the pommel 20 shown in FIG. 1 is pulled gently, while holding the pull tab 22, to move the slider 16 along the connecting strips 12, 14 to join them together by forcing the male zip connector 64 on the second connecting strip 14 into the female zip connector 62 on the first connecting strip 12. Holding the pull tab 22 while zipping the wound closer helps keep the edge connectors taut and prevents the slider from pulling the connecting strips away from the skin at the proximal end 25. FIG. 13 shows the wound after the skin has been trimmed to create a trimmed skin opening 90. FIG. 14 shows the zipped wound closer 10 with the slider 16 located on the closing strips. FIG. 15 shows the zipped wound closer 10 after the slider 16 has been removed, and FIG. 16 shows the zipped wound closer 10 after a clamp 36 has been installed.

The connecting strips 12, 14 can be made of any suitable plastic material with appropriate hardness and flexibility, such as Nylon® or Urethane®, which may be impregnated with Teflon® on the surfaces of the clamp receptacles 66, 68 used by the slider 16 so to reduce surface friction when using the slider to close the connecting strips. The slider 16 may be made from any suitable plastic, such as Acrylic or Polyethylene. The adhesive coating on the bottom surfaces of the flanges 13, 15 of the wound closer may be impregnated with a suitable anaesthetic and an antibiotic or with other required drugs, and may be formed from a microporous substrate that serves as a moisture barrier while allowing air to pass to aid in healing the wound. In the alternative embodiment of FIG. 10, the adhesive bandages 52 may be impregnated with a suitable anaesthetic and an antibiotic or with other required drugs, and may be formed from a microporous substrate that serves as a moisture barrier while allowing air to pass to aid in healing the wound.

The connecting strips of the wound closer may also be manufactured in specific shapes designed for specific surgeries. This may be particularly useful for cosmetic and other common surgeries where the incisions are curved. For example, semicircular wound closers having various diameters may be desirable for mending breast incisions along the edge of the nipple. Appropriately curved wound closers may also be provided for repairing cosmetic surgery incisions along the eyebrow and other curved lines. Similarly, curved wound closers may be desirable for mending curved incisions associated with knee and elbow surgeries.

In view of the foregoing, it will be appreciated that present invention provides significant improvements in wound closing methods and devices. It should be understood that the foregoing relates only to the exemplary embodiments of the present invention, and that numerous changes may be made therein without departing from the spirit and scope of the invention as defined by the following claims.

The invention claimed is:

1. A method for closing and promoting scar-free healing of an opening in living skin tissue, comprising the steps of:
    providing a wound closer having a first elongated connecting strip with an inner face, a second elongated connecting strip having a second inner face, and a slider configured to slide along the first and second connecting strips to zip the connecting strips together to with the first inner face held adjacent to the second inner face;
    adhering the wound closer around the skin opening with the first elongated connecting strip adhered to the skin adjacent to a first side of the skin opening, the second elongated connecting strip adhered to the skin adjacent to a second side of the skin opening, and the first inner face opposing the second inner face;
    trimming the skin along the first connecting strip flush with the first inner face;
    trimming the skin along the second connecting strip flush with the second inner face; and
    promptly after trimming, zipping the connecting strips together to pull the skin opening closed by sliding the slider along the connecting strips to bring the first inner face adjacent to the second inner face and fasten the connecting strips to each other to form a seam holding the skin trimmed along the first and second inner faces together in a butt-joined relation to promote scar-free healing of the skin opening.

2. The method of claim 1, further comprising the steps of:
    providing a knife with a guide follower;
    providing a first knife guide disposed along the first connecting strip;
    trimming the skin along the first connecting strip by placing the guide follower of the knife against the knife guide of the first connecting strip and moving the knife along the first connecting strip while holding the follower against the knife guide;
    providing a second knife guide disposed along the second connecting strip; and a slider configured to slide along the first and second connecting strips to zip the connecting strips together which then remain closed together;
    trimming the skin along the second connecting strip by placing the guide follower of the knife against the knife guide of the second connecting strip and moving the knife along the second connecting strip while holding the knife follower against the knife guide.

3. The device of claim 2, further comprising the steps of:
    configuring each knife guide as an elongated channel extending along the connecting strip and configuring the guide follower as a tab configured to be received within the channel;
    providing one or both of an antibiotic or an anaesthetic substance in the adhesive coating; and
    providing connecting strip that comprise a microporous substrate configured to allow passage of air and prevent seepage of fluid through the seam.

4. The method of claim 1, further comprising the step of providing connecting strips that, when zipped together, form a continuous, toothless water-tight seam to prevent seepage of fluid through the seam.

5. The method of claim 1, further comprising the step of applying a seam sealer to clamp or set an adhesive in the seam.

6. The system of claim 1, further comprising the step of including one or more substances located in the seam formed by the first and second connecting strips that changes color in response to a condition selected from the group comprising:
    the seam being properly closed;
    an adhesive in the seam being properly set;
    application of energy to cure an adhesive in the seam; and
    a passage of time sufficient for wound is healed.

7. The device of claim 1, further comprising the steps of:
    affixing the connecting strips to an adhesive bandage;
    providing one or both of an antibiotic or an anaesthetic substance in the adhesive coating; and
    providing connecting strip that comprise a microporous substrate configured to allow passage of air and prevent seepage of fluid through the seam.

* * * * *